(12) United States Patent
Iijima

(10) Patent No.: US 9,968,423 B2
(45) Date of Patent: May 15, 2018

(54) DENTAL IMPLANT AND SET THEREOF

(71) Applicant: Medical Corporation IT, Chiba (JP)

(72) Inventor: Toshikazu Iijima, Chiba (JP)

(73) Assignee: Medical Corporation IT, Chiba (JP)

( * ) Notice: Subject to any disclaimer, the term of this patent is extended or adjusted under 35 U.S.C. 154(b) by 0 days. days.

(21) Appl. No.: 15/325,328

(22) PCT Filed: Aug. 25, 2015

(86) PCT No.: PCT/JP2015/073859
§ 371 (c)(1),
(2) Date: Jan. 10, 2017

(87) PCT Pub. No.: WO2016/035614
PCT Pub. Date: Mar. 10, 2016

(65) Prior Publication Data
US 2017/0172709 A1    Jun. 22, 2017

(30) Foreign Application Priority Data

Sep. 3, 2014 (JP) .................................. 2014-178639

(51) Int. Cl.
*A61C 8/00* (2006.01)
(52) U.S. Cl.
CPC ................ *A61C 8/00* (2013.01); *A61C 8/005* (2013.01); *A61C 8/0022* (2013.01); *A61C 8/0028* (2013.01); *A61C 8/0072* (2013.01); *A61C 8/0074* (2013.01)

(58) Field of Classification Search
CPC ....... A61C 8/00; A61C 8/0022; A61C 8/0028; A61C 8/005; A61C 8/0072; A61C 8/0074
See application file for complete search history.

(56) References Cited

U.S. PATENT DOCUMENTS

| 5,141,435 | A |   | 8/1992 | Lillard |            |
|-----------|---|---|--------|---------|------------|
| 5,453,007 | A | * | 9/1995 | Wagher  | A61C 8/005 |
|           |   |   |        |         | 433/173    |
| 5,873,721 | A | * | 2/1999 | Willoughby | A61C 8/0001 |
|           |   |   |        |         | 433/172    |
| 5,899,696 | A | * | 5/1999 | Shimoda | A61B 17/666 |
|           |   |   |        |         | 433/172    |
| 5,899,940 | A | * | 5/1999 | Carchidi | A61B 17/666 |
|           |   |   |        |         | 606/305    |

(Continued)

FOREIGN PATENT DOCUMENTS

CN         102240228 A      11/2011

*Primary Examiner* — Nicholas Lucchesi
(74) *Attorney, Agent, or Firm* — Novick, Kim & Lee, PLLC; Jae Youn Kim

(57) ABSTRACT

The present invention provides a dental implant that can deal with a subsequent reduction in bone mass while reducing a burden on a patient, and a set thereof. The present invention is directed to a dental implant comprising: a first stage implant 1 that has a bottomed tubular shape, a male thread 3 formed on an outer periphery thereof, and a female thread 4 formed in an inner periphery thereof; and a second stage implant 2 that has a tip part 6 having a male thread 5 threadably engaged with the female thread 4 of the first stage implant 1 and a rear end part 7 to which an upper prosthesis is to be attached via an abutment 8, wherein the female thread 4 of the first stage implant 1 and the male thread 5 of the second stage implant 2 are tapered threads.

4 Claims, 3 Drawing Sheets

(56) References Cited

U.S. PATENT DOCUMENTS

| | | | | |
|---|---|---|---|---|
| 5,989,025 A | * | 11/1999 | Conley | A61B 17/176 408/241 B |
| 6,126,662 A | * | 10/2000 | Carmichael | A61B 17/666 433/173 |
| 6,213,775 B1 | | 4/2001 | Reipur | |
| 6,537,070 B1 | * | 3/2003 | Stucki-McCormick | A61B 17/666 433/173 |
| 2007/0009854 A1 | * | 1/2007 | Morgan | A61C 8/0022 433/173 |
| 2007/0148621 A1 | | 6/2007 | Yakir | |
| 2008/0261176 A1 | * | 10/2008 | Hurson | A61C 8/0022 433/174 |
| 2011/0189634 A1 | | 8/2011 | Kfir | |
| 2012/0156645 A1 | | 6/2012 | Jacoby | |
| 2014/0148864 A1 | | 5/2014 | Lacaze | |

\* cited by examiner

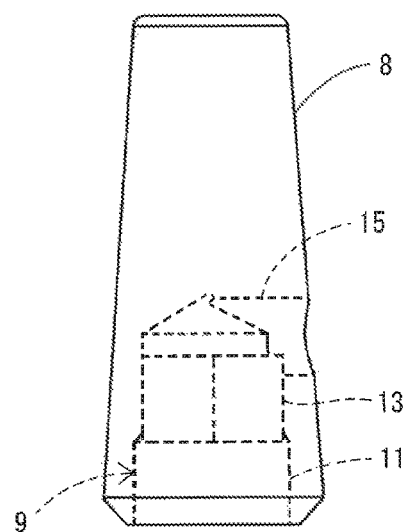
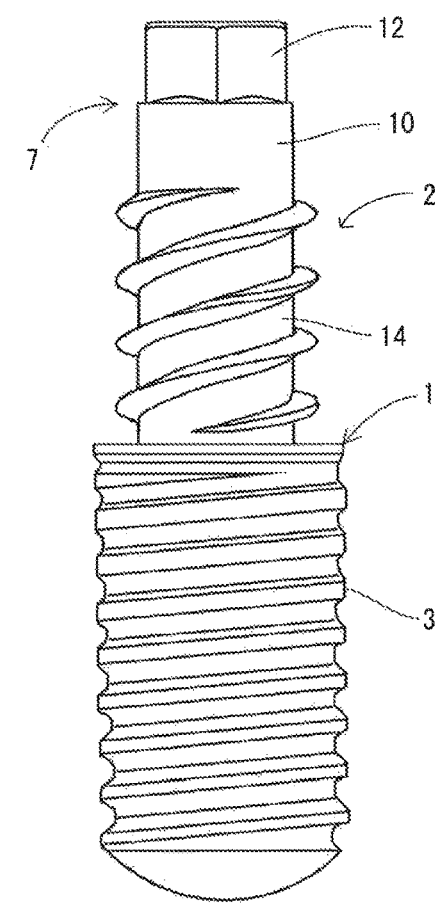
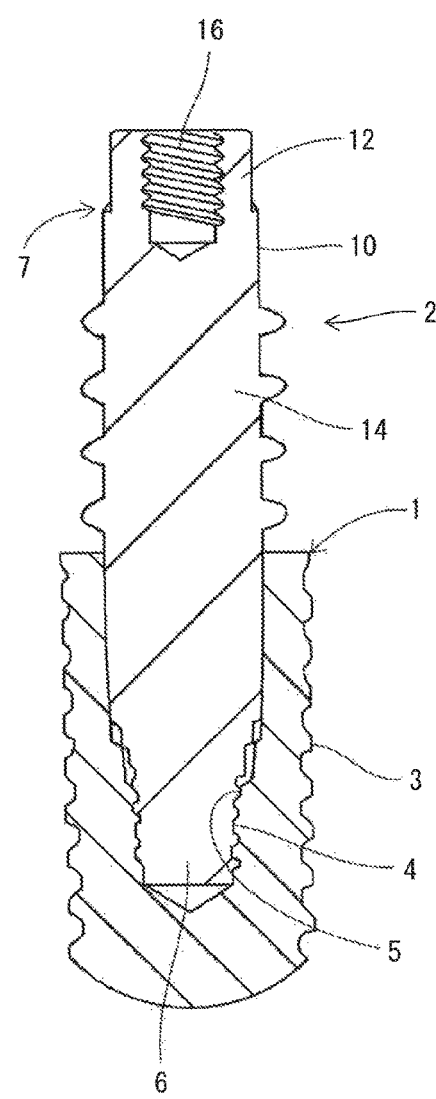
Fig. 1A    Fig. 1B

DENTAL IMPLANT AND SET THEREOF

TECHNICAL FIELD

The present invention relates to a dental implant and a set thereof.

BACKGROUND ART

As shown in FIG. 3, conventional dental implant treatment is typically performed by embedding an implant (fixture) 53 in a drilled hole 52 formed in an alveolar bone 51 in a lost tooth region and attaching an upper prosthesis 55 to the rear end part of the implant 53 via an abutment 54.

SUMMARY OF INVENTION

Technical Problem

However, such conventional dental implant treatment has a problem that the implant 53 is exposed due to a subsequent reduction in bone mass (see the broken line in FIG. 3). In this case, the implant 53 may be again embedded, but a series of second surgery procedures therefore places a heavy burden on a patient.

In light of the above circumstances, it is an object of the present invention to provide a dental implant that can deal with a subsequent reduction in bone mass while reducing a burden on a patient, and a set thereof.

Solutions to Problem

In order to achieve the above object, the present invention is directed to a dental implant comprising: a first stage implant that has a bottomed tubular shape, a male thread formed on an outer periphery thereof, and a female thread formed in an inner periphery thereof; and a second stage implant that has a tip part having a male thread threadably engaged with the female thread of the first stage implant and a rear end part to which an upper prosthesis is to be attached via an abutment, wherein the female thread of the first stage implant and the male thread of the second stage implant are tapered threads.

In the above dental implant, the second stage implant has an intermediate part that is provided between the tip part and the rear end part and that is not covered with any one of the first stage implant, the abutment, and the upper prosthesis, wherein the intermediate part may have an uneven portion formed in an outer periphery thereof.

In order to achieve the above object, the present invention is also directed to a dental implant set comprising: the first stage implant; and two or more second stage implants different from each other in a length of the intermediate part that is provided between the tip part and the rear end part and that is not covered with any one of the first stage implant, the abutment, and the upper prosthesis.

Advantageous Effects of Invention

According to the present invention, it is possible to provide a dental implant that can deal with a subsequent reduction in bone mass while reducing a burden on a patient, and a set thereof.

That is, the dental implant according to any one of claims of the present invention makes it possible to exchange only the second stage implant in a state where the first stage implant remains embedded in a drilled hole formed in alveolar bone. Therefore, for example, even when the second stage implant is exposed due to a subsequent reduction in bone mass, a state where the second stage implant is not exposed can be again achieved by exchanging only the second stage implant for one having a shorter length. In this case, it is not necessary to perform surgery to remove the embedded first stage implant and again form a drilled hole for embedding the first stage implant and the second stage implant, which makes it possible to reduce a burden on a patient.

Further, in the dental implant according to the present invention, the first stage implant and the second stage implant are connected together by the tapered threads. This makes it possible to minimize or eliminate a gap between both the implants and makes it hard for the second stage implant connected to the first stage implant to loosen due to a wedge effect obtained by the tapered threads.

In the dental implant, an uneven portion effective for osseointegration is formed. The uneven portion is advantageous for prevention of inflammation after dental implant treatment as well as engages with part of alveolar bone. Such engagement can function to retard the exposure of the second stage implant (intermediate part) caused by a reduction in bone mass.

BRIEF DESCRIPTION OF DRAWINGS

FIGS. 1A and 1B are respectively front and longitudinal sectional views schematically showing the structure of a dental implant according to an embodiment of the present invention.

DESCRIPTION OF EMBODIMENTS

An embodiment of the present invention will be described below with reference to the drawings.

A dental implant shown in FIGS. 1A and 1B comprises a first stage implant (first stage fixture) 1 and a second stage implant (second stage fixture) 2.

Figure 3:
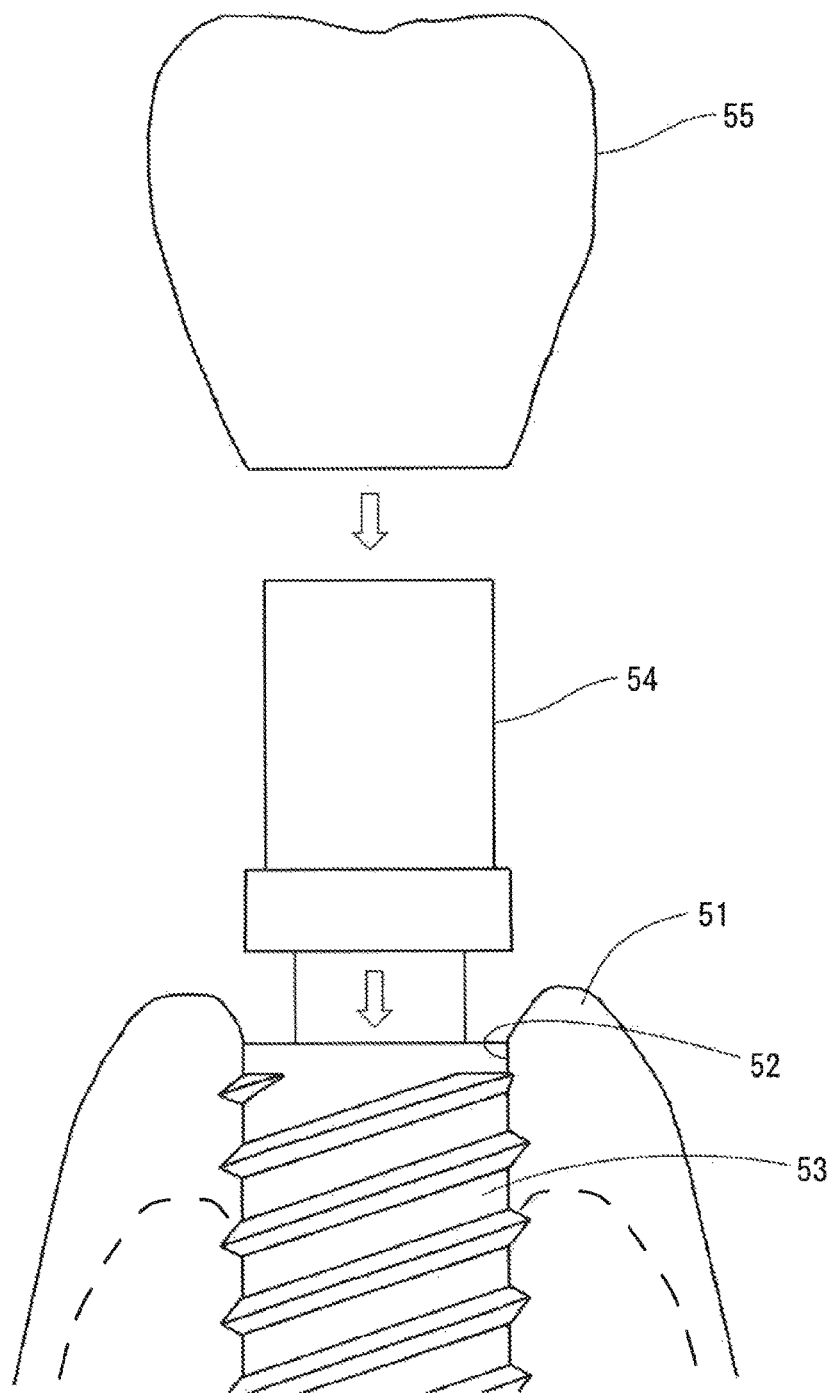
FIG. 3 is an illustration schematically showing a conventional method of dental implant treatment.

The first stage implant 1 is configured to be embedded in a drilled hole 52 (see FIG. 3) formed in alveolar bone 51, and has a bottomed cylindrical shape, a male thread 3 formed in an outer periphery thereof, and a female thread 4 formed in an inner periphery thereof.

The second stage implant 2 is a member having a substantially cylindrical external appearance, and has a tip part 6 having a male thread 5 threadably engaged with the female thread 4 of the first stage implant 1. Further, the female thread 4 of the first stage implant 1 and the male thread 5 of the second stage implant 2 are tapered threads (a taper angle is preferably 6° or less). This makes it possible to minimize or eliminate a gap between the first stage implant 1 and the second stage implant 2 after thread connection and makes it hard for both the threads 4 and 5 after thread connection to loosen due to a wedge effect obtained by the tapered threads.

In the case of the dental implant according to this embodiment, when the first stage implant 1 is embedded in the drilled hole 52, both the first and second stage implants 1 and 2 may be previously integrated together by threadably connecting the second stage implant 2 to the first stage implant 1, or the second stage implant 2 may be threadably connected to the first stage implant 1 after only the first stage implant 1 is embedded in the drilled hole 52.

Then, an upper prosthesis (not shown) is attached to a rear end part 7 of the second stage implant 2 embedded in the drilled hole 52 via an abutment 8. Here, a method for attaching the abutment 8 to the rear end part 7 will be described in detail. As shown in FIG. 1A, the abutment 8 has a vertical hole 9 formed so as to extend from the bottom surface toward the inside thereof. By inserting the rear end part 7 of the second stage implant 2 into the vertical hole 9 from the bottom surface side of the abutment 8, an outer tapered portion 10 of the outer surface of the rear end part 7 of the second stage implant 2 is fitted to an inner tapered portion 11 of the inside of the vertical hole 9 of the abutment 8.

Here, the inner tapered portion 11 slightly increases in diameter toward the bottom surface side, the outer tapered portion 10 is configured to be connected to the inner tapered portion 11 by taper connection (Morse taper connection), and the implants 1 and 2 and the abutment 8 are all made of a metal (e.g., pure titanium or a titanium alloy excellent in biocompatibility, tissue compatibility, and mechanical compatibility) so that a gap is hardly created between the outer tapered portion 10 and the inner tapered portion 11. Therefore, both the outer and inner tapered portions 10 and 11 are in a state where they are strongly connected together by metal-to-metal friction (a state where it is very difficult or impossible to pull out the abutment 8, which is fitted to the second stage implant 2, from the second stage implant 2 with a bare hand).

A taper angle (joint angle) between such outer tapered portion 10 and inner tapered portion 11 may be set to, for example, 0 to 10 degrees. In this embodiment, the taper angle is set to 1.5 degrees so that a strong retentive force generated by taper connection can be ensured. In addition, the surface roughness of both the tapered portions 10 and 11 expressed as, for example, an arithmetic average roughness Ra can be set to 1.6 μm or less (in this embodiment, about 0.26 μm), which makes it possible to reliably obtain a strong retentive force.

Further, at this time, a hexagonal columnar portion 12 of the outer surface of the rear end part 7 of the second stage implant 2 and a hexagonal grooved portion 13 of the inside of the vertical hole 9 of the abutment 8 are engaged with each other to achieve a state in which the rotation of the abutment 8 with respect to the second stage implant 2 is restricted.

The attachment of an upper prosthesis to the abutment 8 can be performed by a known method, and therefore the description thereof will be omitted. The attachment of the upper prosthesis leads to the completion of dental implant treatment using the dental implant according to this embodiment.

Figures 2A, 2B:
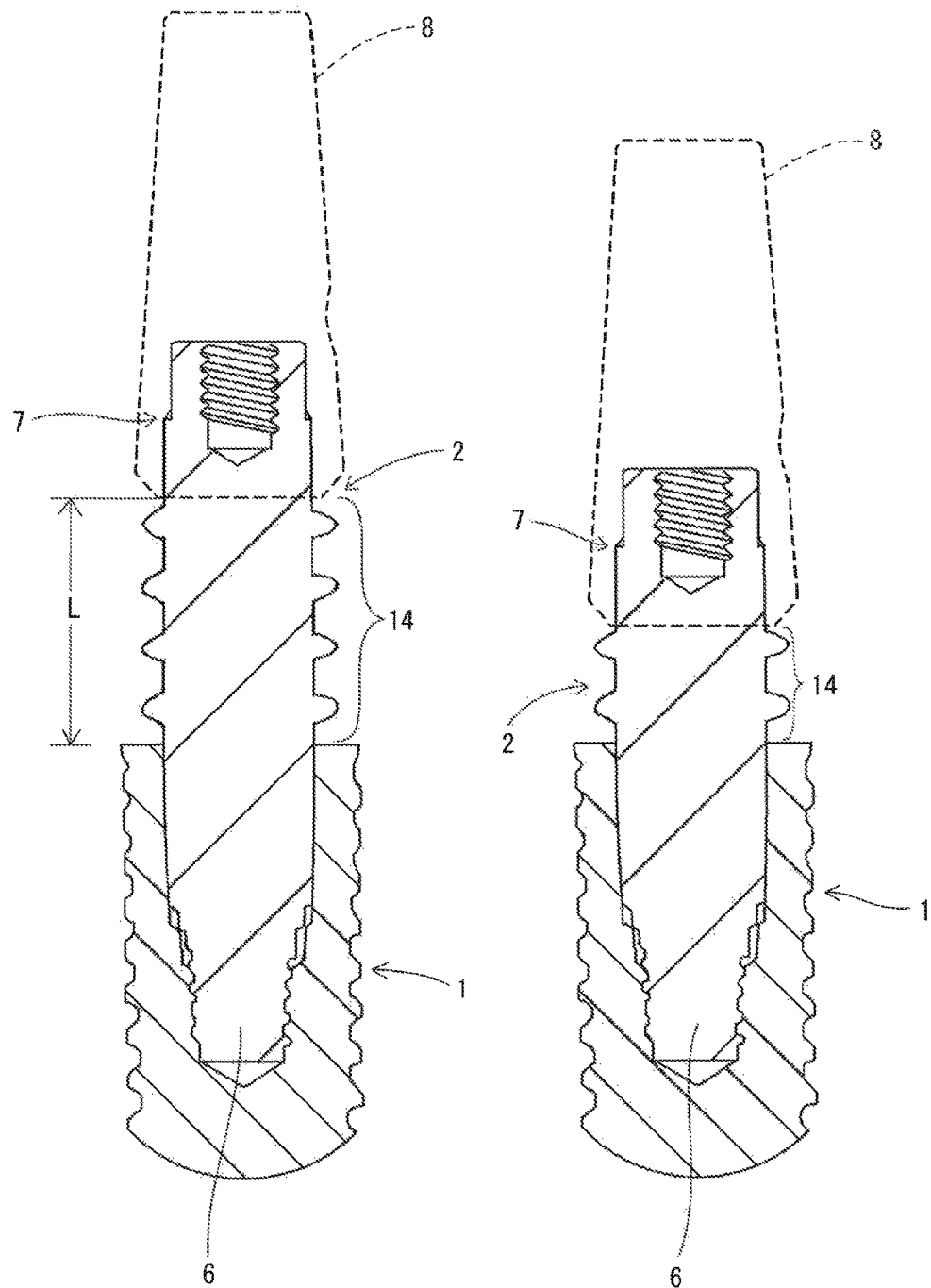
FIGS. 2A and 2B are longitudinal sectional views showing, side by side, two dental implants different in the length of an intermediate part.

Here, as shown in FIG. 2A, an intermediate part 14 not covered with any one of the first stage implant 1, the abutment 8, and the upper prosthesis is provided between the tip part 6 and the rear end part 7 of the second stage implant 2, and almost the entirety of the intermediate part 14 needs to be fitted into the drilled hole 52 when the second stage implant 2 is embedded in the drilled hole 52. Therefore, the drilled hole 52 is formed to be deeper than a conventional one. Further, the drilled hole 52 is formed to have an inner diameter slightly larger than the outer diameter of the second stage implant 2, which, however, does not interfere with osseointegration after surgery.

After embedding of the dental implant, there is a possibility that the intermediate part 14 will be eventually exposed without being covered with the alveolar bone 51 due to a reduction in bone mass. In this case, only the second stage implant 2 of the dental implant shown in FIG. 2A can be exchanged for the second stage implant 2 whose intermediate part 14 has a shorter length L in the axial direction thereof (see FIG. 2B) to again achieve a state where the intermediate part 14 is not exposed. Therefore, it is not necessary to perform surgery to remove the first stage implant 1 and again form the drilled hole 52, which makes it possible to reduce a burden on a patient.

Further, when the second stage implant 2 is exchanged, the abutment 8 externally fitted to the rear end part 7 of the second stage implant 2 needs to be once detached from the rear end part 7. This operation can be performed by, for example, inserting an appropriate tool into a horizontal hole 15 that extends from the side surface toward the inside of the abutment 8 so as to lead to the vertical hole 9.

In the embodiment shown in FIGS. 1A and 1B, the intermediate part 14 has a male threaded portion formed in the outer periphery thereof as an uneven portion effective for osseointegration. In such a case where an uneven portion is formed in the outer periphery of the intermediate part 14, the uneven portion is advantageous for prevention of inflammation after dental implant treatment as well as engages with part of the alveolar bone 51. This engagement can function to retard the exposure of the intermediate part 14 caused by a reduction in bone mass.

It is to be noted that the present invention is not limited to the above embodiment. It is understood that various modifications may be made without departing from the scope of the present invention. For example, the following modifications can be made.

In the embodiment shown in FIGS. 1A and 1B, the intermediate part 14 has a male threaded portion formed in the outer periphery thereof as an uneven portion effective for osseointegration, but the uneven portion is not limited thereto. For example, a roughened surface portion may be provided in the outer periphery of the intermediate part 14 as an uneven portion effective for osseointegration.

As the second stage implant 2, one whose intermediate part 14 has a length L appropriate to a case may be used. Therefore, a set (dental implant set) including two or more second stage implants 2 different from each other in the length L of the intermediate part 14 and at least one first stage implant 1 may be prepared so that the second stage implant 2 can appropriately be selected from the set.

The abutment 8 shown in FIG. 1A is attached to the second stage implant 2 by taper connection. However, the abutment 8 is not limited thereto, and may be, for example, one attached to the second stage implant 2 by a thread member (not shown) threadably engaged with the female threaded portion 16 (see FIG. 1B) formed in the rear end part 7 of the second stage implant 2. Other various known methods may also be employed to attach the abutment 8 to the second stage implant 2.

It goes without saying that the above modifications may be appropriately combined together.

REFERENCE SIGNS LIST

1: first stage implant
2: second stage implant
3: male thread
4: female thread
5: male thread
6: tip part
7: rear end part 8: abutment
9: vertical hole
10: outer tapered portion
11: inner tapered portion
12: hexagonal columnar portion
13: hexagonal grooved portion
14: intermediate part
15: horizontal hole
16: female threaded portion
51: alveolar bone
52: drilled hole
53: implant
54: abutment
55: upper prosthesis

The invention claimed is:

1. A dental implant comprising:
a first stage implant that has a bottomed tubular shape, a male thread formed on an outer periphery thereof, and a female thread formed in an inner periphery thereof; and
a second stage implant that has a tip part having a male thread threadably engaged with the female thread of the first stage implant and a rear end part to which an upper prosthesis is to be attached via an abutment,
wherein the female thread of the first stage implant and the male thread of the second stage implant are tapered threads,
wherein the second stage implant has an intermediate part that is disposed between the tip part and the rear end part and configured not to be covered with any one of the first stage implant, the abutment, and the upper prosthesis, and the intermediate part has an uneven portion formed in an outer periphery thereof,
wherein the uneven portion is configured to engage with part of an alveolar hone, and is male threaded,
wherein the second stage implant is configured to be exchanged with another stage implant while the first stage implant is embedded in the alveolar bone,
wherein the rear end part of the second stage implant includes an outer tapered portion, and the abutment includes a vertical hole disposed inside therein and having an inner tapered portion,
wherein the outer tapered portion of the rear end part is configured to be fitted to the inner tapered portion of the vertical hole by a Morse taper connection, and
wherein the abutment includes a horizontal hole extending from a side surface of the abutment toward the vertical hole disposed inside the abutment.

2. The dental implant of claim 1, wherein the tapered threads have a taper angle of 6° or less.

3. The dental implant of claim 1, wherein a taper angle between the outer tapered portion and the inner tapered portion is 10° or less.

4. A dental implant set comprising: a first stage implant having a bottomed tubular shape, a male thread formed on an outer periphery thereof, and a female thread formed in an inner periphery thereof;
a second stage implant including a first tip part having a first male thread configured to be threadably engaged with the female thread of the first stage implant and a first rear end part to which an upper prosthesis is to he attached via an abutment; and
a third stage implant including a second tip part having a second male thread configured to be threadably engaged with the female thread of the first stage implant and a second rear end part to which the upper prosthesis is to be attached via the abutment,
wherein the female thread of the first stage implant and the male thread of the second or third stage implant are tapered threads, and
wherein each of the second and third stage implants has an intermediate part that is disposed between the respective first and second tip parts and the respective first and second rear end parts, that is configured not to be covered with any one of the first stage implant, the abutment, and the upper prosthesis, and that has an uneven portion formed in an outer periphery thereof,
wherein the intermediate part of the second stage implant is longer than that of the third stage implant in an axial direction thereof,
wherein the second stage implant is configured to be replaced with the third stage implant after the first stage implant is embedded into an alveolar bone and the second stage implant is engaged with the first stage implant,
wherein the rear end part of the second stage implant includes an outer tapered portion, and the abutment includes a vertical hole disposed inside therein and having an inner tapered portion,
wherein the outer tapered portion of the rear end part is configured to be fitted to the inner tapered portion of the vertical hole by a Morse taper connection, and
wherein the abutment includes a horizontal hole extending from a side surface of the abutment toward the vertical hole disposed inside the abutment.

* * * * *